United States Patent
Lee et al.

(10) Patent No.: US 11,676,690 B2
(45) Date of Patent: Jun. 13, 2023

(54) SYSTEM AND METHOD FOR DETECTION OF SYNTHESIZED VIDEOS OF HUMANS

(71) Applicant: NURALOGIX CORPORATION, Toronto (CA)

(72) Inventors: Kang Lee, Toronto (CA); Evgueni Kabakov, North York (CA); Winston De Armas, Toronto (CA); Alan Ding, North Vancouver (CA); Darshan Singh Panesar, Toronto (CA)

(73) Assignee: NURALOGIX CORPORATION, Toronto (CA)

( * ) Notice: Subject to any disclaimer, the term of this patent is extended or adjusted under 35 U.S.C. 154(b) by 0 days.

(21) Appl. No.: 17/627,285

(22) PCT Filed: Jun. 30, 2020

(86) PCT No.: PCT/CA2020/050913
§ 371 (c)(1),
(2) Date: Jan. 14, 2022

(87) PCT Pub. No.: WO2021/007652
PCT Pub. Date: Jan. 21, 2021

(65) Prior Publication Data
US 2022/0262148 A1 Aug. 18, 2022

Related U.S. Application Data

(60) Provisional application No. 62/875,761, filed on Jul. 18, 2019.

(51) Int. Cl.
*G16H 10/60* (2018.01)
*G16H 30/40* (2018.01)
(Continued)

(52) U.S. Cl.
CPC .......... *G16H 10/60* (2018.01); *A61B 5/0261* (2013.01); *A61B 5/7267* (2013.01); *G06N 20/00* (2019.01);
(Continued)

(58) Field of Classification Search
None
See application file for complete search history.

(56) References Cited

U.S. PATENT DOCUMENTS 11,320,902 B2 * 5/2022 Lee .................. A61B 3/113
11,471,083 B2 * 10/2022 Lee .................. G06N 3/0445
(Continued)

FOREIGN PATENT DOCUMENTS

CN 103049766 A 4/2013
CN 103251391 A 8/2013
(Continued)

OTHER PUBLICATIONS

International Search Report of the International Searching Authority for application No. PCT/CA2020/050913 dated Jun. 30, 2020.
(Continued)

*Primary Examiner* — Leon Flores
(74) *Attorney, Agent, or Firm* — Bhole IP Law; Anil Bhole; Marc Lampert

(57) ABSTRACT

A system and method for detection of synthesized videos of humans. The method including: determining blood flow signals using a first machine learning model trained with a hemoglobin concentration (HC) changes training set, the first machine learning model taking as input bit values from a set of bitplanes in a captured image sequence, the HC changes training set including bit values from each bitplane of images captured from a set of subjects for which HC changes are known; determining whether blood flow patterns from the video are indicative of a synthesized video
(Continued)

using a second machine learning model, the second machine learning model taking as input the blood flow signals, the second machine learning model trained using a blood flow training set including blood flow data signals from at least one of a plurality of videos of other human subjects for which it is known whether each video is synthesized.

20 Claims, 8 Drawing Sheets

(51) Int. Cl.

| | | |
|---|---|---|
| *G06N 20/00* | (2019.01) | |
| *G06V 10/82* | (2022.01) | |
| *G06V 40/40* | (2022.01) | |
| *G06V 20/00* | (2022.01) | |
| *G06V 10/774* | (2022.01) | |
| *A61B 5/026* | (2006.01) | |
| *A61B 5/00* | (2006.01) | |
| *G06V 10/42* | (2022.01) | |
| *G06V 40/16* | (2022.01) | |
| *G06V 40/10* | (2022.01) | |

(52) U.S. Cl.
CPC .......... *G06V 10/431* (2022.01); *G06V 10/774* (2022.01); *G06V 10/82* (2022.01); *G06V 20/95* (2022.01); *G06V 40/161* (2022.01); *G06V 40/172* (2022.01); *G06V 40/40* (2022.01); *G16H 30/40* (2018.01); *G06V 40/15* (2022.01)

(56) References Cited

U.S. PATENT DOCUMENTS

2018/0199870 A1    7/2018  Lee et al.
2018/0314879 A1*  11/2018  Khwaja ................ A61B 5/349

FOREIGN PATENT DOCUMENTS

| CN | 103793690 A | 5/2014 |
|---|---|---|
| CN | 107908928 A | 4/2018 |
| CN | 109069072 A | 12/2018 |
| CN | 109558813 A | 4/2019 |
| WO | 2018232717 A1 | 12/2018 |

OTHER PUBLICATIONS

Written Opinion of the International Searching Authority for application No. PCT/CA2020/050913 dated Jun. 30, 2020.
Conotter, V., et al., "Physiologically-based detection of computer generated faces in video", 2014 IEEE International Conference on Image Processing (JCJP), Oct. 27-30, 2014, pp. 248-252, ISSN 2381-8549 [online] [retrieved on Sep. 23, 2020 (Sep. 23, 2020)]. https://doi.org/10.1109/icip.2014.7025049.
First Office Action for Chinese application No. 202080064673.7, Chinese Patent Office, dated: Dec. 7, 2022.
Conotter, V., et al., "Physiologically-based detection of computer generated faces in video", 2014 IEEE International Conference on Image Processing (ICIP), Paris, France, 2014, pp. 248-252, doi: 10.1109/ICIP.2014.7025049.

* cited by examiner

SYSTEM AND METHOD FOR DETECTION OF SYNTHESIZED VIDEOS OF HUMANS

TECHNICAL FIELD

The following relates generally to digital video processing and more specifically to a system and method for detection of synthesized videos of humans.

BACKGROUND

A recent technological emergence is that artificial video of a human's face can be synthesized from two or more component videos. These artificial videos are commonly referred to as "DeepFakes" because these videos generally involve human image synthesis using "deep learning" (artificial computer-based learning) techniques to superimpose one video onto another. This can involve replacing the face of one human subject in a video with the face of another human subject in a seamless and photorealistic manner, resulting in a synthesized or DeepFake video. Creating a DeepFake video can alternatively involve creating an artificial video of an individual from other videos of that individual. DeepFake videos can be deceitful in nature, for example used for the purposes of defamation, misinformation, and the like; however, detecting such synthesized videos is a substantial technical challenge in the art.

SUMMARY

In an aspect, there is provided a method for detection of synthesized videos of humans, the method executed on one or more processors, the method comprising: receiving a video comprising a captured image sequence of light re-emitted from the skin of a human subject; determining blood flow signals using a first machine learning model trained with a hemoglobin concentration (HC) changes training set, the first machine learning model taking as input bit values from a set of bitplanes in the captured image sequence, the HC changes training set comprising bit values from each bitplane of images captured from a set of subjects for which HC changes are known; determining whether blood flow patterns from the video are indicative of a synthesized video using a second machine learning model, the second machine learning model taking as input the blood flow signals, the second machine learning model trained using a blood flow training set comprising blood flow data signals from at least one of a plurality of videos of other human subjects for which it is known whether each video is synthesized; and outputting the determination of whether the blood flow patterns from the video are indicative of a synthesized video.

In a particular case of the method, the second machine learning model further takes as input physiological information, and wherein the blood flow training set further comprises physiological information from at least one of the plurality of videos of other human subjects for which it is known whether each video is synthesized.

In another case of the method, determining the blood flow signals comprises determining a blood flow signal for each of a plurality of predetermined regions of interest (ROIs) of the human subject captured by the images based on the HC changes.

In yet another case of the method, the bit values from the set of bitplanes in the captured image sequence comprises the bit values that are determined to approximately maximize a signal-to-noise ratio (SNR).

In yet another case of the method, the second machine learning model outputs a statistical probability corresponding to a level of certainty of whether the blood flow patterns from the video are indicative of a synthesized video.

In yet another case of the method, the method further comprising decomposing the blood flow signals outputted by the first machine learning model into a frequency profile and a phase profile, the frequency profile and the phase profile used as the input blood flow signals to the second machine learning model.

In yet another case of the method, the frequency profile comprises a frequency spectrum analysis per ROI.

In yet another case of the method, the frequency profile comprises separately defined frequency passband signals over the frequency spectrum, wherein each frequency passband signal comprises an individual 12th order Elliptical digital filter.

In yet another case of the method, the frequency profile comprises a combination of discrete frequency passband signals.

In yet another case of the method, the phase profile comprises a plurality of beat vectors, each beat vector comprising motion of a blood flow signal in a particular ROI relative to the blood flow signal in another ROI.

In another aspect, there is provided a system for detection of synthesized videos of humans, the system comprising one or more processors and a data storage device, the one or more processors configured to execute: a TOI module to receive a video comprising a captured image sequence of light re-emitted from the skin of a human subject and to determine blood flow signals using a first machine learning model trained with a hemoglobin concentration (HC) changes training set, the first machine learning model taking as input bit values from a set of bitplanes in the captured image sequence, the HC changes training set comprising bit values from each bitplane of images captured from a set of subjects for which HC changes are known; a machine learning module to determine whether blood flow patterns from the video are indicative of a synthesized video using a second machine learning model, the second machine learning model taking as input the blood flow signals, the second machine learning model trained using a blood flow training set comprising blood flow data signals from at least one of a plurality of videos of other human subjects for which it is known whether each video is synthesized; and an output module to output the determination of whether the blood flow patterns from the video are indicative of a synthesized video.

In a particular case of the system, the second machine learning model further takes as input physiological information, and wherein the blood flow training set further comprises physiological information from at least one of the plurality of videos of other human subjects for which it is known whether each video is synthesized.

In another case of the system, determining the blood flow signals by the TOI module comprises determining a blood flow signal for each of a plurality of predetermined regions of interest (ROIs) of the human subject captured by the images based on the HC changes.

In yet another case of the system, the bit values from the set of bitplanes in the captured image sequence comprises the bit values that are determined to approximately maximize a signal-to-noise ratio (SNR).

In yet another case of the system, the second machine learning model outputs a statistical probability corresponding to a level of certainty of whether the blood flow patterns from the video are indicative of a synthesized video.

In yet another case of the system, the system further comprising a profile module to decompose the blood flow signals outputted by the first machine learning model into a frequency profile and a phase profile, the frequency profile and the phase profile used as the input blood flow signals to the second machine learning model.

In yet another case of the system, the frequency profile comprises a frequency spectrum analysis per ROI.

In yet another case of the system, the system further comprising a filter module to separately defined frequency passband signals over the frequency spectrum as the frequency profile, wherein each frequency passband signal comprises an individual 12th order Elliptical digital filter.

In yet another case of the system, the system further comprising a combination module to combine discrete frequency passband signals as the frequency.

In yet another case of the system, the phase profile comprises a plurality of beat vectors, each beat vector comprising motion of a blood flow signal in a particular ROI relative to the blood flow signal in another ROI.

These and other aspects are contemplated and described herein. It will be appreciated that the foregoing summary sets out representative aspects of embodiments to assist skilled readers in understanding the following detailed description.

BRIEF DESCRIPTION OF THE DRAWINGS

The features of the invention will become more apparent in the following detailed description in which reference is made to the appended drawings wherein.

DETAILED DESCRIPTION

Figure 1:
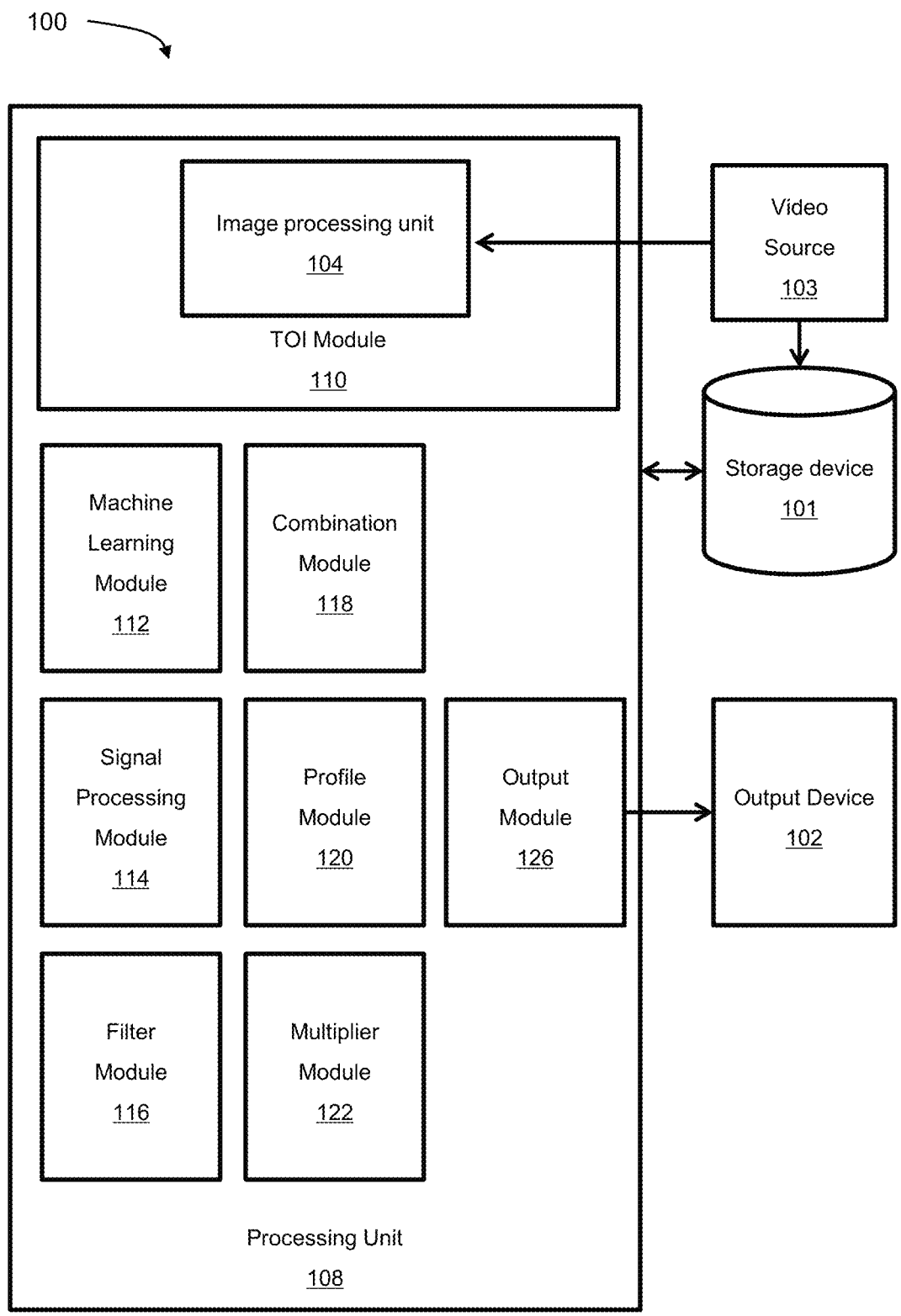
FIG. 1 is a block diagram of a system for detection of synthesized videos of humans, according to an embodiment.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

The following relates generally to digital video processing and more specifically to a system and method for detection of synthesized videos of humans.

Approaches for identifying synthesized videos can involve deconstruction and evaluation of video features such as resolution, noise, and frame rate. Some of these approaches can use deep learning models to identify and evaluate such video features for abnormalities (for example, misaligned frames, blurriness in specific regions of the video, changes in resolution within the videos) and then report the likelihood that the face in the video is not an original recording. However, these approaches are generally lengthy, inaccurate, and need to be continually updated to accommodate new video synthesis techniques and technologies.

The present embodiments can use remote video photoplethysmography to identify synthesized videos. In this way, light passes through the skin and into superficial blood vessels. Specific wavelengths of light are absorbed by hemoglobin in the blood as its concentration oscillates with the cardiac cycle. These small attenuations of ambient light emanating from the skin are captured by a video camera and the data for which is stored as a video. This video is processed, as described herein, to determine a blood flow signal reflecting hemoglobin concentration. For the case of synthesized videos, these blood flow signals can contain abnormalities arising from merging two distinct blood flows into a single video; for example, discontinuities in blood flow oscillations or other signal distortions. Advantageously, such abnormalities can be used to identify synthetic videos.

Advantageously, identifying synthetic videos by processing of these blood flow signals is generally less computationally resource intensive and significantly faster than other approaches.

In embodiments of the system and method described herein, technical approaches are provided to solve the technological problem of identifying a synthesized video by determining whether a given blood flow pattern in a given video is from a single human source or synthesized from multiple sources. These human-synthetic blood flow patterns are quantified using image processing techniques performed over a plurality of images captured within a video. Advantageously, such analysis can occur relatively rapidly.

The technical approaches of the present embodiments advantageously utilize body specific data driven machine-trained models that are executed against an incoming video stream and/or file. In some cases, the incoming video stream is a series of images of the human facial area. In other cases, the incoming video stream can be a series of images of any human body extremity with exposed vascular surface area (e.g., devoid of hair); for example, the face, arm, and hand. In most cases, each captured body extremity requires separately trained models. For the purposes of the following disclosure, reference will be made to capturing the human's face within a video; however, it will be noted that other areas can be used with the approaches described herein.

Referring now to FIG. 1, a system for detection of synthesized videos of humans 100, according to an embodiment, is shown. The system 100 includes a processing unit 108, one or more video sources 103, a storage device 101, and an output device 102. The processing unit 108 may be communicatively linked to the storage device 101, which may be preloaded, periodically loaded, and/or continuously loaded with video imaging data obtained from one or more video sources 103, for example, video files. The processing unit 108 includes various interconnected elements and modules, including a TOI module 110, a machine learning module 112, a signal processing module 114, a first filter module 116, a combination module 118, a profile module 120, a multiplier module 122, and an output module 126. The TOI module 110 includes an image processing unit 104. In some cases, the image processing unit 104 receives the videos from the one or more video sources 103 directly. The video images captured by an image capture device can be stored as a video file (which in some cases, may refer to a plurality of images strung together in a sequence forming a video). This video file can be located in a database at the video source 103; and in some cases, the camera can be the video source 103. The videos can be processed by the image processing unit 104 and stored on the storage device 101. In further embodiments, one or more of the modules can be executed on separate processing units or devices, including the video source 103 or output device 102. In further embodiments, some of the features of the modules may be combined, executed on other modules, or executed remotely. In some cases, the system 100 and the camera can be collocated on a device; for example, a smartphone or laptop.

Figure 3:
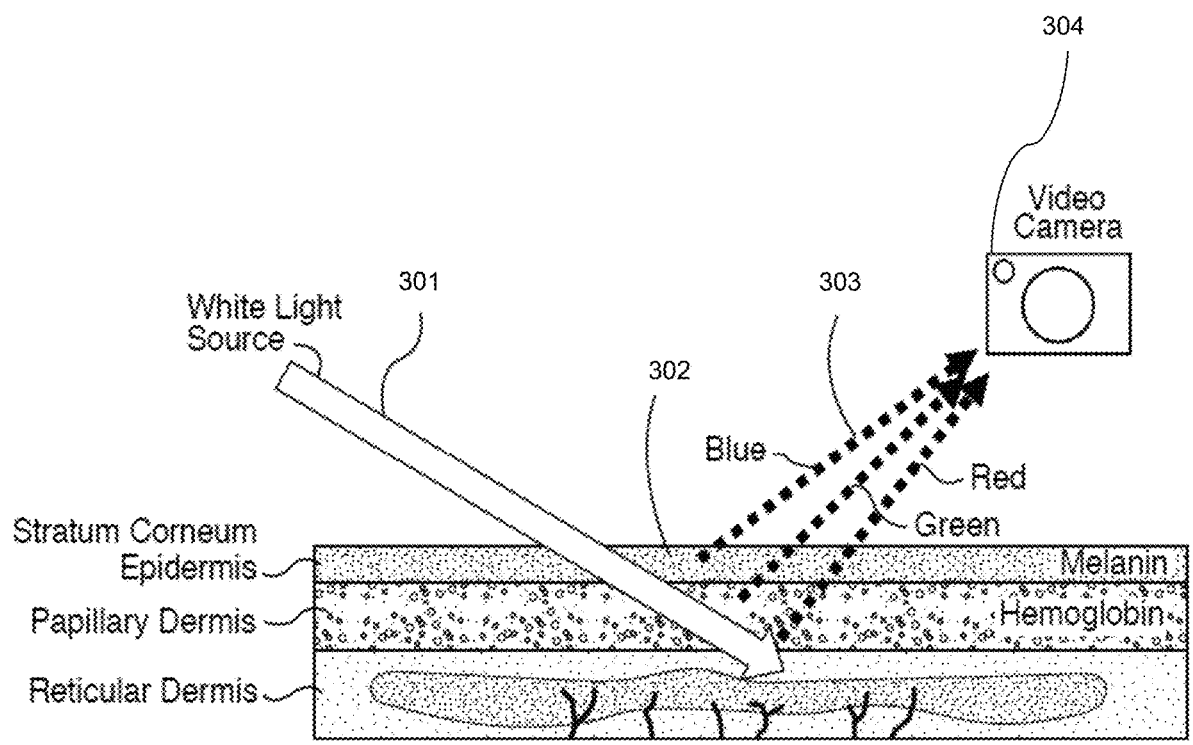
FIG. 3 is a diagram of an example of re-emission of light from skin epidermal and subdermal layers.
Figure 4:
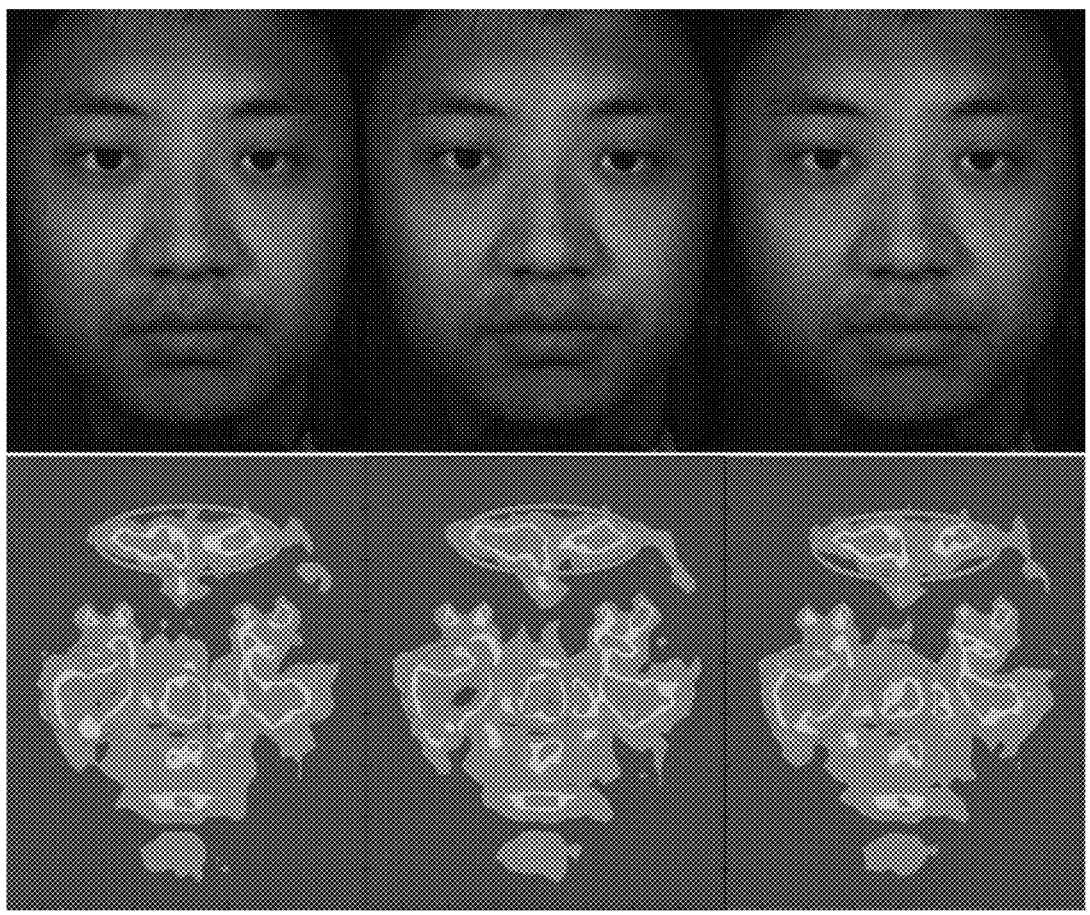
FIG. 4 is a set of example surface and corresponding transdermal images illustrating change in hemoglobin concentration for a particular human subject at a particular point in time.

Using transdermal optical imaging (TOI), the TOI module 110 can isolate hemoglobin concentration (HC) from raw images received from the video source 103. Referring now to FIG. 3, a diagram illustrating the re-emission of light from skin is shown. Light 301 travels beneath the skin 302, and re-emits 303 after travelling through different skin tissues. The re-emitted light 303 may then be captured by a camera 304 and the resulting image files are stored at the video source 103. The dominant chromophores affecting the re-emitted light are melanin and hemoglobin. Since melanin and hemoglobin have different color signatures, it has been found that it is possible to obtain images mainly reflecting HC under the exposed (hairless) epidermis as shown in FIG. 4.

Using transdermal optical imaging (TOI), the TOI module 110, via the image processing unit 104, obtains each captured image in a video stream and/or video-file 103, and performs operations upon the image to generate a corresponding optimized hemoglobin concentration (HC) image of the subject. From the HC data, the blood flow localized volume concentrations can be determined. The image processing unit 104 isolates HC in the captured video sequence. In an exemplary embodiment, the images of the human subject's faces are taken at 30 frames per second. It will be appreciated that the image sequences used by the TOI module 110 can be from a wide variety of video sources; thus, include a variety of resolutions, lighting conditions, and frame rates.

In a particular case, isolating HC can be accomplished by the TOI module 110 by analyzing bitplanes in the sequence of video images to determine and isolate a set of the bitplanes that approximately maximize signal to noise ratio (SNR). The determination of high SNR bitplanes is made with reference to a first training set of images constituting the captured video-file sequence(s), in conjunction with human-synthesized blood flow pattern data gathered from real and synthesized videos with human subjects. The determination of high SNR bitplanes is made with reference to an HC training set constituting the captured video sequence.

Figure 8:
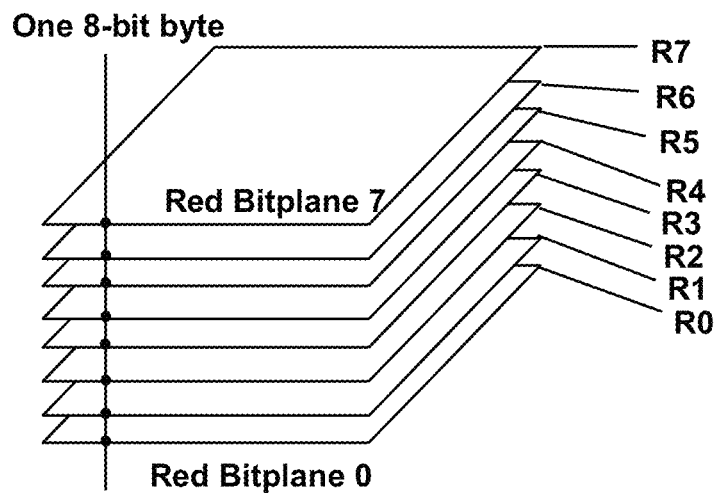
FIG. 8 is an example illustration of bitplanes for a three channel image.
Figure 8:
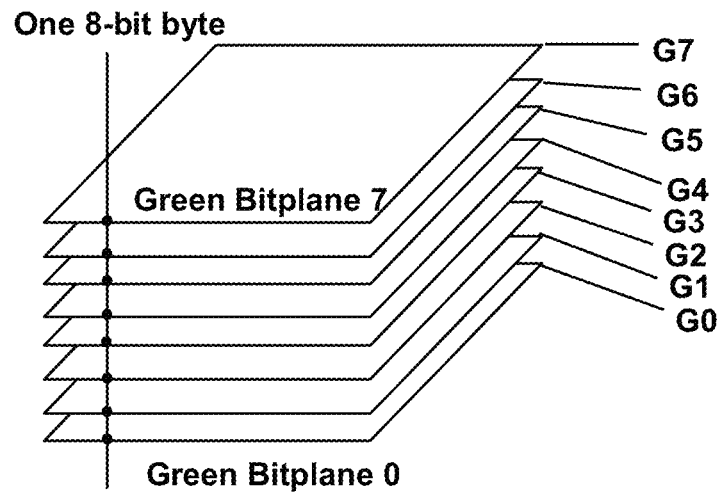
Figure 8:
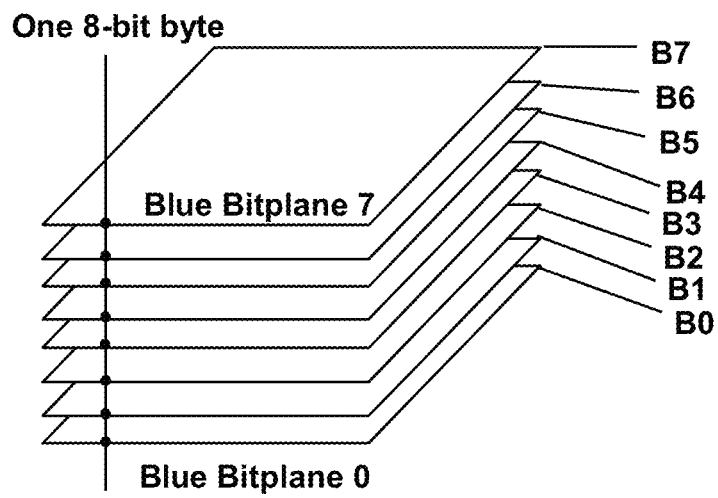

Bitplanes are a fundamental aspect of digital images. Typically, a digital image consists of certain number of pixels (for example, a width×height of 1920×1080 pixels). Each pixel of the digital image having one or more channels (for example, color channels red, green, and blue (RGB)). Each channel having a dynamic range, typically 8 bits per pixel per channel, but occasionally 10 bits per pixel per channel for high dynamic range images. Whereby, an array of such bits makes up what is known as the bitplane. In an example, for each image of color videos, there can be three channels (for example, red, green, and blue (RGB)) with 8 bits per channel. Thus, for each pixel of a color image, there are typically 24 layers with 1 bit per layer. A bitplane in such a case is a view of a single 1-bit map of a particular layer of the image across all pixels. For this type of color image, there are therefore typically 24 bitplanes (i.e., a 1-bit image per plane). Hence, for a 1-second color video with 30 frames per second, there are at least 720 (30×24) bitplanes. FIG. 8 is an exemplary illustration of bitplanes for a three-channel image (an image having red, green and blue (RGB) channels). Each stack of layers is multiplied for each channel of the image; for example, as illustrated, there is a stack of bitplanes for each channel in an RGB image. In the embodiments described herein, Applicant recognized the advantages of using bit values for the bitplanes rather than using, for example, merely the averaged values for each channel. Thus, a greater level of accuracy can be achieved for making predictions of HC changes, and thus synthesized video determinations, as disclosed herein. Particularly, a greater accuracy is possible because employing bitplanes provides a greater data basis for training a first machine learning model, as described herein.

TOI signals can be taken from regions of interest (ROIs) of the human subject, for example nose, cheeks, ears, forehead, or other exposed skin areas and can be defined manually or automatically for the video images. The ROIs are preferably non-overlapping. These ROIs are preferably selected on the basis of which HC is particularly indicative of measurement of HC change patterns. Using the native images that consist of all bitplanes of all three R, G, B channels, signals that change over a particular time period (for example, 10 seconds) on each of the ROIs are extracted.

Parts of a signal where motion has been detected using computer vision or other means may be removed and the remaining parts of the signal recombined to produce a continuous signal without concurrent motion.

The raw signals can be pre-processed using one or more filters by the filter module 116, depending on the signal characteristics. Such filters may include, for example, a Butterworth filter, a Chebyshev filter, or the like. Using the filtered signals from two or more ROIs, machine learning is employed to systematically identify bitplanes that will significantly increase the signal differentiation (for example, where the SNR improvement is greater than 0.1 db) and bitplanes that will contribute nothing or decrease the signal differentiation. After discarding the latter, the remaining bitplane images can optimally determine blood flow generally associated with a determination of whether a given blood flow pattern is from a single human source or synthesized from multiple sources.

For passing to a first machine learning model, the TOI module 110 can first manipulate the bitplane vectors (for example, 24 bitplanes×60 hz) using the bit value in each pixel of each bitplane along the temporal dimension. In one embodiment, this can involve subtraction and addition of each bitplane to maximize the signal differences in ROIs over the time period. In some cases, the addition or subtraction can be performed in a pixel-wise manner. In some cases, to obtain reliable and robust machine learning models, the training data for the first machine learning model can be divided into three sets: a training set (for example, 80% of the whole subject data), a test set (for example, 10% of the whole subject data), and an external validation set (for example, 10% of the whole subject data). Generally, the time period of the training data can vary depending on the length of the raw data (for example, 15 seconds, 60 seconds, or 120 seconds). The first machine learning model can use any suitable machine learning technique; for example, using a Long Short Term Memory (LSTM) neural network, Gaussian Process Inference Networks (GPNet), or other types of Artificial Neural Networks (ANN). The machine learning technique for the first machine learning model can be selected based on accuracy and efficiency in, for example, determining improvement of differentiation in terms of accuracy, which bitplane(s) contributes the best information, and which bitplane(s) does not in terms of feature selection.

In an embodiment using the Long Short Term Memory (LSTM) neural network, the TOI module 110 can perform group feature selections and classifications. In this way, the TOI module 110 can obtain a set of bitplanes to be isolated from image sequences to reflect temporal changes in HC. In some cases, the TOI module 110 can use an image filter to isolate the identified bitplanes, as described herein. In this way, the first machine learning model can be used to assess the existence of common spatial-temporal patterns of hemoglobin changes across subjects (for example, differences in amplitude in blood flow changes in the forehead and the cheek over time).

Blood flow data can be determined from HC change data using the pixels of each of the images as a function of time. In some cases, to increase signal-to-noise ratio (SNR), the human's face or other region of skin can be divided into a plurality of regions of interest (ROIs). The division can be according to, for example, the human's differential underlying physiology, such as by the autonomic nervous system (ANS) regulatory mechanisms. In this way, data in each ROI can be averaged. The ROIs can be manually selected or automatically detected with the use of a face tracking software or other region of interest tracking software. The machine learning module 112 can then average the data in each ROI. This information can then form the basis for the training set. As an example, the system 100 can monitor stationary HC changes contained by a selected ROI over time, by observing (or graphing) the resulting temporal profile (for example, shape) of the selected ROI HC intensity values over time. In some cases, the system 100 can monitor more complex migrating HC changes across multiple ROIs by observing (or graphing) the spatial dispersion (HC distribution between ROIs) as it evolves over time.

Thus, the system 100 can receive a video sequence of a human subject and apply the HC extracted from selected bitplanes to a second machine learning model to determine blood flow, generally associated with a particular subject, to make a determination of whether videos are synthesized. For long running video streams with changes in blood flow and intensity fluctuations, changes of the estimation and intensity scores over time relying on HC data based on a moving time window (e.g., 10 seconds) may be used.

In an example using the Long Short Term Memory (LSTM) neural network, the LSTM neural network comprises at least three layers of cells. The first layer is an input layer, which accepts the input data. The second (and perhaps additional) layer is a hidden layer, which is composed of memory cells (see the diagrammatic example of FIG. 5). The final layer is output layer, which generates the output value based on the hidden layer using Logistic Regression.

Figure 5:
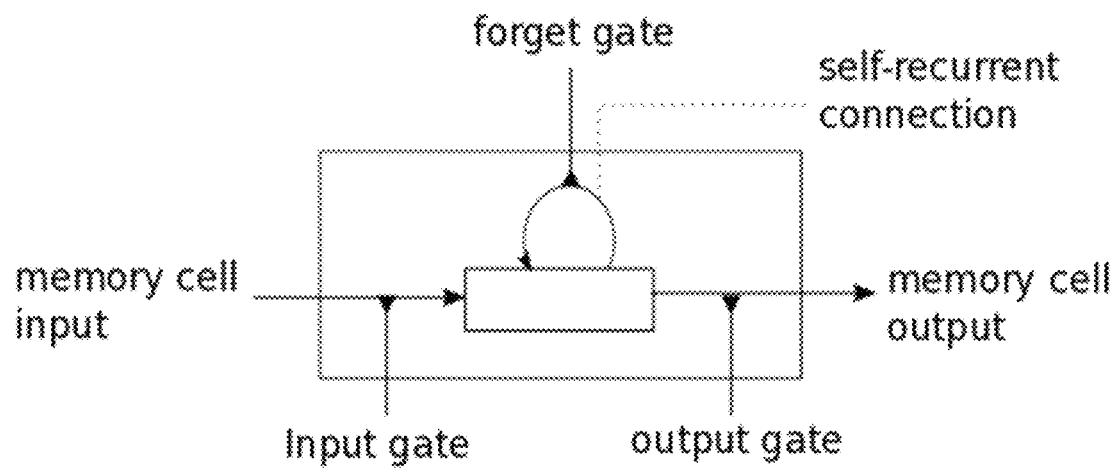
FIG. 5 is a diagrammatic representation of an example memory cell.

Each memory cell, as illustrated in FIG. 5, comprises four main elements: an input gate, a neuron with a self-recurrent connection (a connection to itself), a forget gate and an output gate. The self-recurrent connection has a weight of 1.0 and ensures that, barring any outside interference, the state of a memory cell can remain constant from one time step to another. The gates serve to modulate the interactions between the memory cell itself and its environment. The input gate permits or prevents an incoming signal to alter the state of the memory cell. On the other hand, the output gate can permit or prevent the state of the memory cell to have an effect on other neurons. Finally, the forget gate can modulate the memory cell's self-recurrent connection, permitting the cell to remember or forget its previous state, as needed.

The equations below describe how a layer of memory cells is updated at every time step t. In these equations:

$x_t$, is the input array to the memory cell layer at time t. In our application, this is the blood flow signal at all ROIs:

$$\hat{x}_t = [x_{1t} x_{2t} \ldots x_{nt}]$$

$W_i$, $W_f$, $W_c$, $W_o$, $U_i$, $U_f$, $U_c$, $U_o$, and $V_o$ are weight matrices; and $b_i$, $b_f$, $b_c$ and $b_o$ are bias vectors.

The values for $i_t$, the input gate, and $C_t$, the candidate value for the states of the memory cells are determined at time t:

$$i_t = (W_i w_t + U_i h_{t-1} + b_i)$$

$$\tilde{C}_t = \tanh(W_c x_t + U_c h_{t-1} + b_c)$$

The value for $f_t$, the activation of the memory cells forget gates at time t, is determined:

$$f_t = (W_f x_t + U_f h_{t-1} + b_f)$$

Given the value of the input gate activation in the forget gate activation $i_t$, the forget gate activation f and the candidate state value $C_t$, $C_t$, the memory cells' new state at time t, can be determined:

$$C_t = i_t * \tilde{C}_t + f_t * C_{t-1}$$

With the new state of the memory cells, the value of their output gates and, subsequently, their outputs, can be determined:

$$o_t = (W_o x_t + U_o h_{t-1} + V_o C_t + b_o)$$

$$h_t = o_t * \tanh(C_t)$$

Based on the model of memory cells, for the blood flow distribution at each time step, the system 100 can determine the output from memory cells. Thus, from an input sequence $x_1, x_2, x_3, \ldots, x_n$, the memory cells in the LSTM layer will produce a representation sequence $h_0, h_1, h_2, \ldots, h_n$.

In some cases, a goal can be to classify the sequence into different conditions. A Logistic Regression output layer can generate the probability of each condition based on the representation sequence from the LSTM hidden layer. The vector of the probabilities at time step t can be calculated using softmax by:

$$p_t = \text{softmax}(W_{output} h_t + b_{output})$$

The machine learning module 112 uses the dynamic changes, over time, of localized blood-flow localized volume concentrations at each of the regions-of-interest (ROI) determined by the TOI module 110 to quantify blood flow patterns to determine if the video has been synthesized. In order to determine blood flow patterns that are indicative of synthesized videos, the machine learning module 112 uses a second machine learning model to produce a predictive estimate that the blood flow pattern is from a synthesized video. The second machine learning model takes as input the HC change data from the TOI module 110 and passes it through the trained second machine learning model; and in some cases, combined with continuous real-time extraction of features from the dynamic observed behaviour of the subject's measured blood flow. In this way, the system 100 determines blood flow signals from hemoglobin concentration changes, for example, in different regions of interest, using the first machine learning model. Features can be extracted from the blood flow signal. With such features as input, the second machine learning model can be used to predict whether the video is synthesized.

The process of machine learning, by the machine learning module 112, allows for the generation of probabilistic mappings or multi-dimensional transfer-functions between the extracted bio-signals from the TOI module 110 presented as training input, as described herein, and the resultant blood flow pattern estimates for determining synthetic videos, as the outputs. To train the second machine learning model, the machine learning module 112 systematically receives TOI data from a plurality of training videos with human subjects. In some cases, the human subjects used for training preferably meet certain stratification criteria for the specific population study.

During training of the second machine learning model, by the machine learning module 112, TOI videos of a plurality of videos of humans and videos of humans that are synthesized are respectively received. In some cases, these training videos can be received under controlled circumstances and with accompanying "ground truth" information alongside (as described herein). In some cases, the machine learning models can be trained with increasing robustness as the diversity of the humans used for training increases. Preferably, the plurality of human subjects used for training covers a diverse spectrum of ages, genders, cultural origins, skin tones, and the like. Preferably, the plurality of humans used for training have a variety of levels for varying physiologies (e.g., hypotensive to hypertensive in the case of blood pressure), and high proportion of real and synthetic videos.

In an embodiment of the system 100, the second machine learning model can be generated according to a supervised training process; where a "ground truth" level of a given blood flow pattern is labelled as a target condition and a variety of training examples are used to train the model. In some cases, the training examples can be fed into the second machine learning model sequentially in rounds of training. The training examples are prepared from the human dataset by the techniques described herein. These techniques utilize advanced data-science machine learning architectures, for example Multi-Level Perceptron and Deep (hierarchical) Neural Networks, which are capable of 'deciphering' non-obvious relationships from large datasets to make predictive outcomes. In some cases, the accuracy of the blood flow pattern estimates, and their use as a prediction of synthesized videos, from such models is linearly proportional to the quantity and quality of the training dataset.

In some cases, for increasing the accuracy of the second machine learning model regarding the relationships between blood flow data (as input) and determinations of whether the video is synthesized (as output), and for reducing the time to arrive at training convergence, the system 100 can leverage domain knowledge to enhance the quality of the input data. Such domain knowledge can include certain attributes, qualities or features of the input data, collected by the profile module 120, that can be consequential to increasing the accuracy of the relationship between the input and the output; for example, systolic rising time, amplitude of systolic peak, amplitude of dicrotic notch, dicrotic notch time, and pulse pressure. Using such domain knowledge as further input into the second machine learning model during training can increase the accuracy of the second machine learning model's predictions; for example, due to exaggeration by the certain attributes, qualities or features of the domain knowledge.

Figure 2:
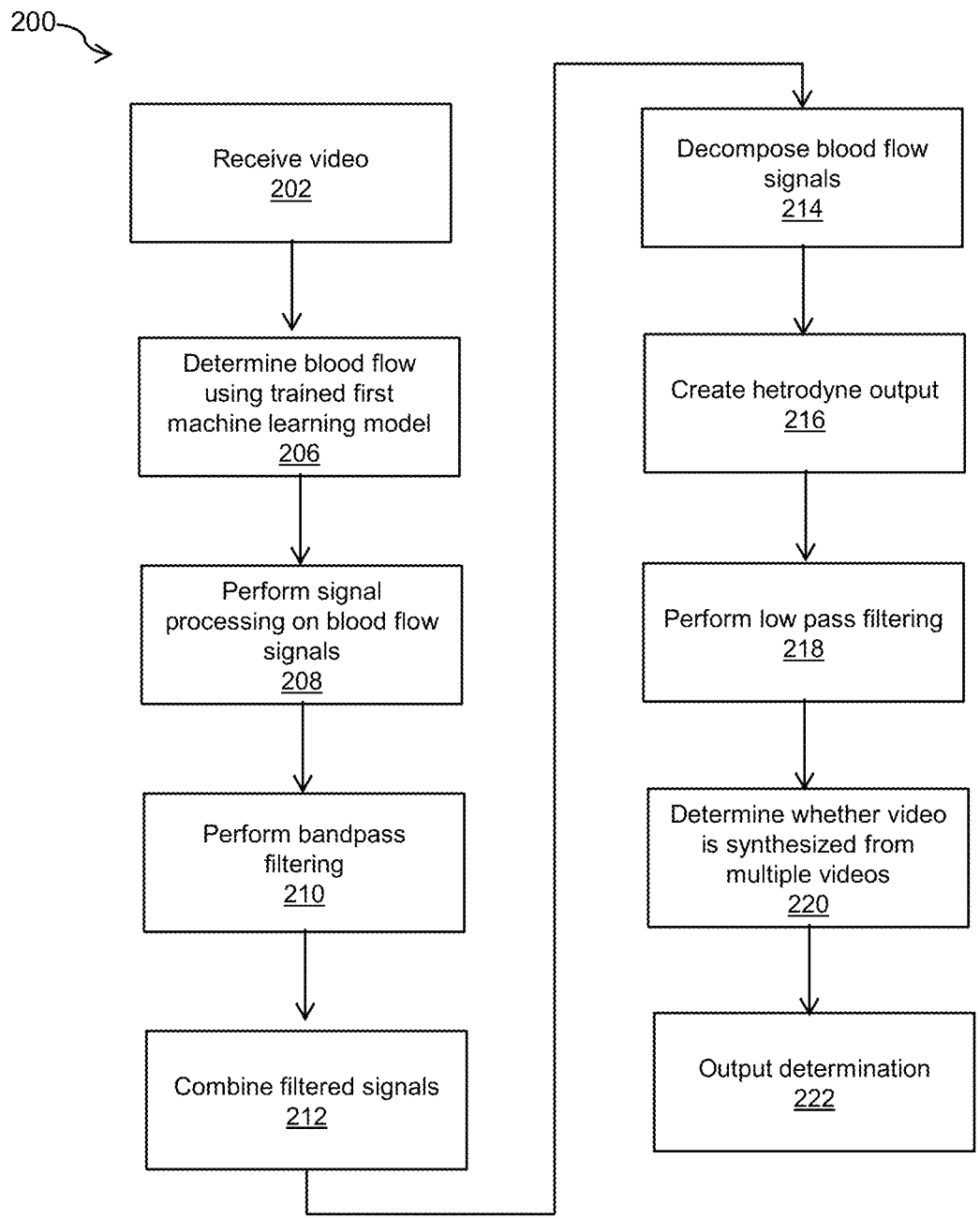
FIG. 2 is a flowchart for a method for detection of synthesized videos of humans, according to an embodiment.

Turning to FIG. 2, a flowchart for a method for detection of synthesized videos of humans 200, according to an embodiment, is shown.

At block 202, the TOI module 110 receives a video comprising one or more images from the video source 103.

At block 206, blood flow is determined from the video using the first machine learning model by the TOI module 110, as described herein. In some cases, the blood flow is determined for localized volume concentrations at defined regions-of-interest (ROI) on the subject's face. Using the temporal sequence of images comprising the video, the TOI module 110 can record dynamic changes of such localized volume concentrations over time.

In an example, the subject's face can be divided into 'm' different regions of interest. In this case, there will be 'm' separate ROI signals, each processing a unique signal extracted from each image of the video. The grouping of these 'm' ROI signals is collectively referred to as a bank of ROI signals.

Figure 6:
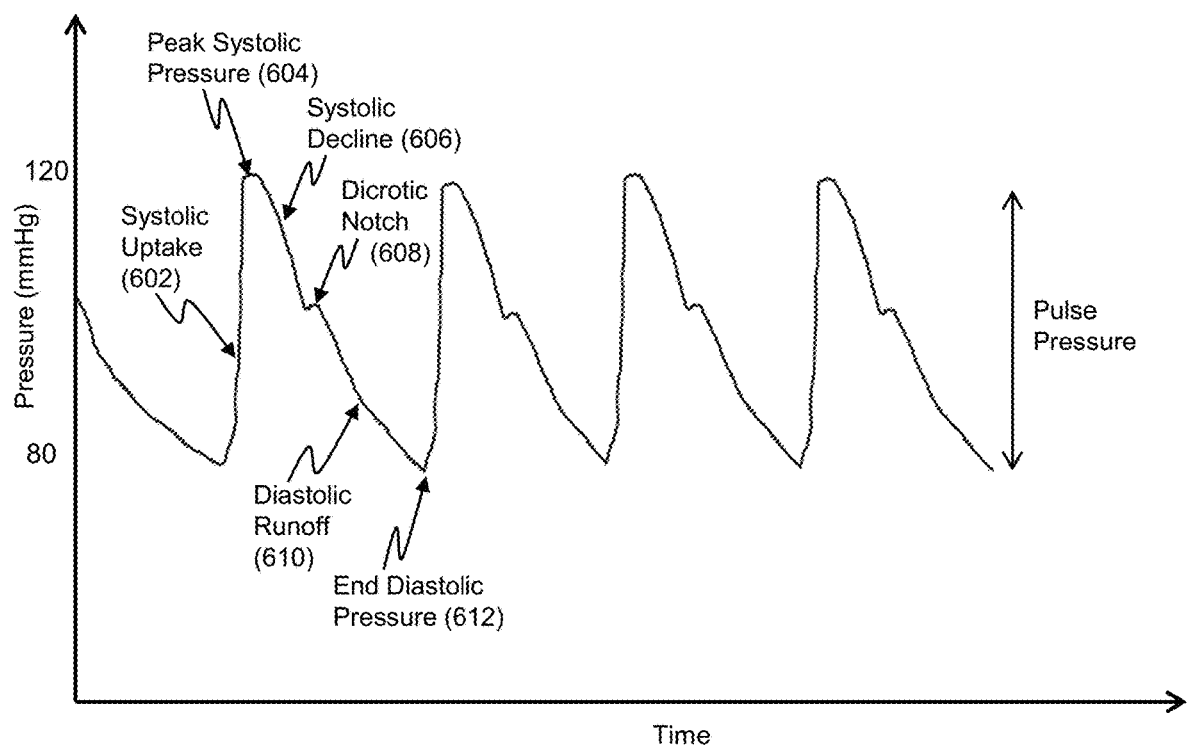
FIG. 6 is graph illustrating an exemplary blood flow signal generated by the system of FIG. 1.

FIG. 6 illustrates an exemplary signal magnitude (y-axis), measured as a function of time (x-axis), outputted by the TOI module 110 for a particular ROI. As shown, the present inventors advantageously recognized that the signal extracted from the TOI module 110 can at least partially resemble an exemplary signal taken from an inter-arterial blood pressure monitor and resemble features of pressure pulses. In this case, while the TOI signal may be somewhat noisier than the signal extracted from the inter-arterial blood pressure monitor, the pertinent characteristics of the signal can be extracted and thus used to train the second machine learning model; for example, characteristics like systolic uptake 602, peak systolic pressure 604, systolic decline 606, dichrotic notch 608, diastolic runoff 610, and end diastolic pressure 612. In an example, the characteristics can be extracted by denoising the signal with signal processing techniques as described herein. In this example, the denoised signal can be detrended to remove fluctuations in the signal baseline over time. In this example, the signal can then be segmented into pulses by detecting a major frequency in a given area of signal. Features can then be extracted from the pulses; for example, global minima/maxima, local minima/maxima, slopes, amplitudes, rates of change, and the like.

At block 208, in some cases, the blood flow volume data from each ROI is processed by the signal processing module 114. In some cases, the blood flow volume data from each ROI can be treated as an independent signal and routed through a corresponding processing path. In this way, multiple ROIs each generate signals which are independently, yet concurrently, processed by the signal processing module 114 using digital signal processing (DSP) techniques. DSP techniques may include, for example, digital filters (e.g., high-pass, low-pass, band-pass), Fourier transforms (time and frequency domains), wavelet transforms (time-frequency domain), and the like. Such DSP techniques may be useful for removing high frequency noise inherent to the signal acquisition process, removing low and ultra-low frequency oscillations of physiological origin that naturally occur within humans (e.g., Mayer waves), and the like. The TOI module 110 generates quantity 'm' uniquely defined ROIs superimposed over the image, whose boundaries are preferably non-overlapping in area. In other cases, the ROI boundaries may be overlapping.

At block 210, the filter module 116 analyzes 'n' separately defined frequency passbands over the image frequency spectrum received from the signal processing module 114. The spectral energy within each passband is measured by utilizing a narrowband digital filter with 'bandpass' (BPF) characteristics. Each of the resultant bandpass signals is called a "BPF signal" or "BPF instance". In this way, each bandpass filter implements a passband consisting of crisply defined lower and upper frequency specification, where a gain (within the passband range) is preferably much greater than a provided attenuation (outside the passband range).

In a particular case, the filter module 116 can construct each BPF signal as an individual 12th order Elliptical digital filter. Each filter preferably has identical bandpass start/stop and gain/attenuation characteristics but, differing in configured start/stop 'edge' frequencies. The filter module 116 advantageously uses this high-order filter architecture to balance the requirements for a steep roll-off magnitude characteristic with minimal phase distortion. In some cases, the passband 'start' frequency is configurable. In some cases, the passband range (span) is fixed for every BPF at 0.1 Hz; as an example, meaning that the 'end' frequency will be calculated as the 'start' frequency plus 0.1 Hz.

In some cases, at block 212, the combination module 118 combines a set of 'n' discrete BPF instances. In this way, a large contiguous frequency range can be covered by assigning stepwise increasing 'start' frequencies to each BPF instance. Each BPF signal can thus operate on a portion of the image available frequency spectrum. Deployment of progressive assignments for the BPF 'start' frequencies can ensure approximately complete coverage of the spectrum; as an example, between 0.1 Hz and 6.0 Hz, with a granularity of 0.1 Hz, yielding a total of 60 BPF instances. In these cases, each ROI signal, of quantity 'm' in total, will have a locally designated BPF set, of quantity 'n' BPF signals in total, to divide and process the frequency spectrum of the ROI signal, as described above. This aggregation of narrowband filters is collectively referred to as a "filter bank".

In some cases, at block 214, the profile module 120 decomposes the ROI signals, acquired across multiple ROIs, to generate a multi-dimensional frequency profile (also called a magnitude profile) and a phase profile (also called a timing profile or velocity profile). The magnitude profile and the timing profile can be used as features (input) to the second machine learning model by the machine learning module 112. This "feature engineering" can advantageously be used to enhance the effectiveness of the machine learning training process by increasing the useful input data for differentiating blood flow pattern determinations for determining synthetic videos; and thus, have a higher accuracy at identifying blood flow patterns of synthesized videos.

In the present embodiment, domain knowledge determined by the profile module 120 can include the magnitude profile to enhance an attribute of the blood flow input data. In the case of the magnitude profile, a distribution of frequency information across the blood flow data (per ROI) has been determined by the present inventors to have significance to the estimation of blood flow pattern indicative of synthesized videos. As such, as described below, a frequency spectrum analysis per ROI, in this case using fixed banks of digital filters, is performed. The digital filters' signals provide a real-time frequency spectrum of the time-domain signal; comparable to performing fast Fourier transform (FFT) but on every frame. An intended advantage of using digital filters is to create 'n' individual frequency filtered streams that can be manipulated and/or routed independently to build the second machine learning model. The analysis is thus then provided to the second machine learning model to enhance the accuracy of determining whether the video is synthesized.

In some cases, a beat signal can be used to derive an indication of motion of one ROI blood flow signal relative to another ROI blood flow signal; where the frequency of the resultant beat signal is proportional to a difference in blood flow velocity (known as the heterodyne effect). A beat vector can be created for each ROI against some or all of the other ROIs (eliminating any redundant pairs); whereby this collection of beat vectors can be considered the timing profile. In some cases, the timing profile can be constantly updated at fixed intervals. As such, the timing profile can represent an overall complex interference pattern which is based on the differences in blood flow velocities. Therefore, the timing profile can be provided to the second machine learning model to emphasize blood flow velocity in order to enhance the accuracy of determining whether the video is synthesized.

In these cases, the magnitude profile includes 'n' discrete points which span the range from the low to the high end of the analyzed spectrum. The magnitude profile is generated by the profile module 120 by creating a single summing junction F(i), where T represents a frequency step or positional index for summation of quantity 'm' total BPF outputs associated with the frequency step T. Each magnitude point, F(i) represents a measure of the narrowband spectral energy summed across 'm' separate ROIs.

In some cases, the profile module 120 can construct the timing profile 'P' from quantity 's' slices, with each P(s) slice representing the sum of all possible pair combinations of quantity 'm' total BPF outputs associated with the frequency step T. In some cases, the potential pairings are reduced to eliminate redundant combinations.

In some cases, at block 216, the pair combinations, or remaining unique pair combinations, are routed to a multiplier module 122, representing a multiplier junction at index 'k', to create a new 'hetrodyne' output signal H(i, k), which is determined via multiplication of signals from different inputs. For each frequency step T, the 'k' index will range through ((m×(m−1))/2) total junctions. P(s) therefore represents the summation of H(i,k) for a given step T. There are quantity 'n' slices of output signals H(i, k) in total to cover the entire spectrum of BPF filters.

In some cases, at block 218, the filter module 116 can further process the 'P' profile by a low pass filter (LPF). In this way, the filter module 116 can remove the sidebands created in the heterodyne alterations while providing a quantifying measure to the 'beat' signal energy resulting from the signal pairings.

In some cases, the machine learning module 112 can utilize selective configurations, such as those configured by a trainer, of the temporal (time changing) features provided by the magnitude profile and the frequency profile to create individually trained model(s), each emphasizing different training characteristics. As described herein, these numerically derived features can also be combined with one or more physiological biosignals that are determined from the TOI blood-flow data; for example, heart-rate, heart rate variability, Mayer wave, and other low or ultra-low frequency arterial oscillations which are naturally occurring and continuously present within the human, and the like.

Both the features outputted by the filter module 116 and the recovered biosignals (physiological) from the TOI module 110 can be used to a priori train the second machine learning model, as described above, and, at block 220, in a posteriori determinations of blood flow patterns indicative of synthesized videos. At block 222, the output module 126 can out the determinations of the machine learning module 112; for example, as data to the storage device, as data sent to other systems over a network, or displayed to a user via an output device 102.

The trained second machine learning model uses training examples that comprise known inputs (for example, TOI blood flow data) and known outputs (ground truths) of blood flow patterns from known synthesized videos and/or known non-synthesized videos. The relationship being approximated by the machine learning model is TOI blood-flow data to estimates of blood flow patterns and physiological signals in synthesized videos; whereby this relationship is generally complex and multi-dimensional. Through iterative machine learning training, such a relationship can be outputted as vectors of weights and/or coefficients. The trained second machine learning model being capable of using such vectors for approximating the input and output relationship between TOI blood flow input and estimated output of the blood flow pattern indicative of whether a given blood flow pattern is from a single video of a human subject or synthesized from multiple video sources. In some cases, the multiple video sources can include multiple subjects, or in other cases, may include multiple videos of a single subject.

The ground truth data for the second machine learning model can include a binary determination of whether or not a video used for training is synthesized (i.e., fake). The videos used to train the second machine learning model generally have a known ground truth; such that it is known whether they are synthesized. In this way, in some cases, the second machine learning model can act as a classifier trained to predict whether features from the blood flow input data is from a synthesized input video or not.

In an embodiment, the system 100 uses the magnitude profile F(i) to transform the TOI input data stream from the TOI module 110 into frequency domain values, while (in some cases, concurrently) uses the timing profile P(i) to transform the same TOI input data stream into difference, or 'beat', signals between pairs of data streams. In some cases, the magnitude profile F(i) can be generated (transformed) by digital filter banks. In this case, TOI time-series input signals are received and an output is generated into separate frequency 'bins'. The above is referred to as a transform because it is comparable in effect to executing a Fast-Fourier-Transform (FFT) on every single frame. This approach is advantageous because it is much simpler to execute time-domain digital filters, in addition to the fact that it is possible to manipulate or route each output stream independently. In other cases, instead of digital filter banks, the magnitude profile F(i) can be generated using a hardware implementation; for example, using a hardware based field-programmable gate array (FPGA) FFT module. In some cases, the per frame output from a bank of digital filters is comparable to the per frame FFT output of the same digital input signal.

The frequency domain values and the beat signals can be used as input features and passed to the second machine learning model to further refine the model and therefore provide enhanced accuracy for determining whether the video is synthesized.

Figure 7:
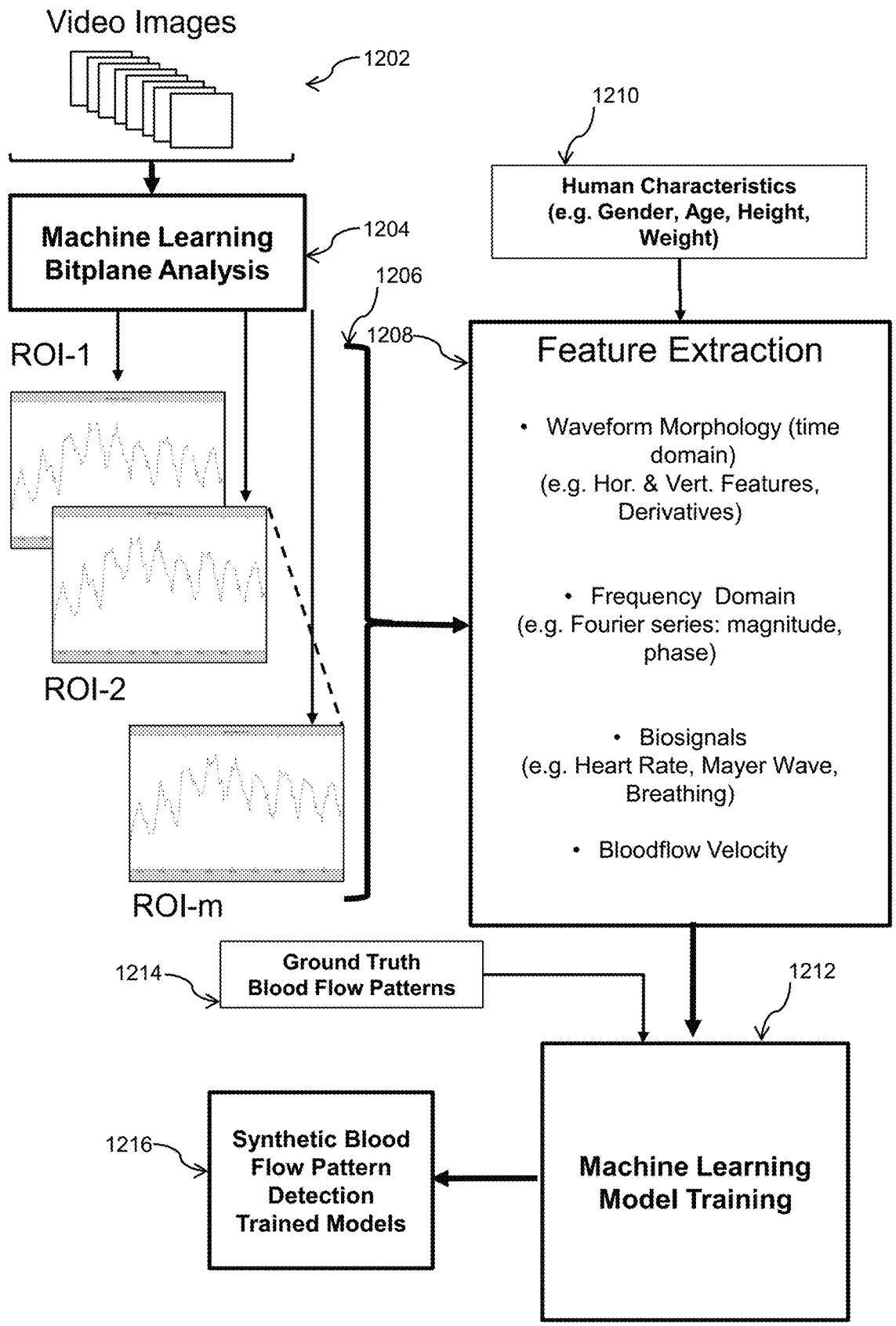
FIG. 7 is an example flowchart illustrating an example implementation of the embodiment of FIG. 1.

FIG. 7 illustrates an exemplary implementation of the embodiments described herein. The TOI module 110 receives a set of images 1202 from a video of the human subject. Using the first machine learning model, the TOI module 110 performs bitplane analysis 1204 on the set of images 1202 to arrive at TOI signals 1206 for each ROI. In some cases, in order to increase accuracy of the blood flow pattern determination; the determination of whether a given blood flow pattern is from a single video source or synthesized from multiple sources. In some cases, the TOI module 110 can perform feature extraction 1208 on each of the TOI signals for each ROI to feed into the second machine learning model, as described herein. Feature extraction 1208 can include, for example, determining waveform morphology features of the signals; such as, horizontal (time) and vertical (HC) features of the waves, derivatives of the signals, or the like. Feature extraction 1208 can also include, for example, determining frequency domain features of the signals; such as, magnitude and phase of a Fourier series of the signals, or the like. Feature extraction 808 can also include, for example, determining physiological features of the signals; such as, heart rate, Mayer waves, heart rate variability, or the like. Feature extraction 1208 can also include, for example, determining blood-flow velocity based on the signals. In some cases, human characteristics 1210 (for example, age, height, weight, sex, skin colour, or the like) of the human subjects can be used to inform the feature extraction 1208. The second machine learning model can then be trained 1212 by the machine learning module 112 based on the bitplane data per ROI 1206, in some cases in conjunction with the feature extraction 1208, to determine whether blood flow pattern data is synthesized from multiple videos. The machine learning model can be, for example, a convolutional neural network (CNN), a deep neural network (DNN), a multilayer perceptron (MLP), or the like. In some cases, the accuracy of the training of the second machine learning model can be aided by ground truth data of whether blood flow pattern comes from an original video or synthetic video 1214. Using the trained second machine learning model, the system 100 can make prediction 1216 about whether the blood flow patters are from a single video source or synthesised from multiple videos.

The output of the second machine learning model is a classification of whether the input video was "synthesized" or "not synthesized". In some cases, the second machine learning model also outputs a statistical probability of how certain the model is of this classification. Level of certainty (as a proportion from 0 to 1) for each class in a binary classification model can be determined using a Softmax function. The desired proportion is multiplied by 100 to get a percentage. For example, a probability of 0.64 can be outputted that a classification as "synthesized" was correct. In some cases, the statistical probability may be displayed to the user (for example, as 64% certainty). In some cases, the statistical probabilities may be adjusted based on other information; for example, based on SNR.

Embodiments of the present disclosure can be applied, for example, for detecting synthetized videos in electronic databases, television, social media, news, and the like. Embodiments of the present disclosure can thus be used to identify instances of fake, forged, misrepresented, deceptive, fraudulent, and/or simulated videos of various persons.

In addition, embodiments of the present disclosure can be used, for example, as a tool by courts, law enforcement, and investigative scientists for the detection of synthesized videos; for example, in the examination of evidence.

Other applications may become apparent.

Although the invention has been described with reference to certain specific embodiments, various modifications thereof will be apparent to those skilled in the art without departing from the spirit and scope of the invention as outlined in the claims appended hereto. The entire disclosures of all references recited above are incorporated herein by reference.

The invention claimed is:

1. A method for detection of synthesized videos of humans, the method executed on one or more processors, the method comprising:
   receiving a video comprising a captured image sequence of light re-emitted from the skin of a human subject;
   determining blood flow signals using a first machine learning model trained with a hemoglobin concentration (HC) changes training set, the first machine learning model taking as input bit values from a set of bitplanes in the captured image sequence, the HC changes training set comprising bit values from each bitplane of images captured from a set of subjects for which HC changes are known;
   determining whether blood flow patterns from the video are indicative of a synthesized video using a second machine learning model, the second machine learning model taking as input the blood flow signals, the second machine learning model trained using a blood flow training set comprising blood flow data signals from at least one of a plurality of videos of other human subjects for which it is known whether each video is synthesized; and
   outputting the determination of whether the blood flow patterns from the video are indicative of a synthesized video.

2. The method of claim 1, wherein the second machine learning model further takes as input physiological information, and wherein the blood flow training set further comprises physiological information from at least one of the plurality of videos of other human subjects for which it is known whether each video is synthesized.

3. The method of claim 1, wherein determining the blood flow signals comprises determining a blood flow signal for each of a plurality of predetermined regions of interest (ROIs) of the human subject captured by the images based on the HC changes.

4. The method of claim 3, further comprising decomposing the blood flow signals outputted by the first machine learning model into a frequency profile and a phase profile, the frequency profile and the phase profile used as the input blood flow signals to the second machine learning model.

5. The method of claim 4, wherein the frequency profile comprises a frequency spectrum analysis per ROI.

6. The method of claim 5, wherein the frequency profile comprises separately defined frequency passband signals over the frequency spectrum, wherein each frequency passband signal comprises an individual 12th order Elliptical digital filter.

7. The method of claim 6, wherein the frequency profile comprises a combination of discrete frequency passband signals.

8. The method of claim 4, wherein the phase profile comprises a plurality of beat vectors, each beat vector comprising motion of a blood flow signal in a particular ROI relative to the blood flow signal in another ROI.

9. The method of claim 1, wherein the bit values from the set of bitplanes in the captured image sequence comprises the bit values that are determined to approximately maximize a signal-to-noise ratio (SNR).

10. The method of claim 1, wherein the second machine learning model outputs a statistical probability corresponding to a level of certainty of whether the blood flow patterns from the video are indicative of a synthesized video.

11. A system for detection of synthesized videos of humans, the system comprising one or more processors and a data storage device, the one or more processors configured to execute:
   a Transdermal Optical Imaging (TOI) module to receive a video comprising a captured image sequence of light re-emitted from the skin of a human subject and to determine blood flow signals using a first machine learning model trained with a hemoglobin concentration (HC) changes training set, the first machine learning model taking as input bit values from a set of bitplanes in the captured image sequence, the HC changes training set comprising bit values from each bitplane of images captured from a set of subjects for which HC changes are known;
   a machine learning module to determine whether blood flow patterns from the video are indicative of a synthesized video using a second machine learning model, the second machine learning model taking as input the blood flow signals, the second machine learning model trained using a blood flow training set comprising blood flow data signals from at least one of a plurality of videos of other human subjects for which it is known whether each video is synthesized; and an output module to output the determination of whether the blood flow patterns from the video are indicative of a synthesized video.

12. The system of claim 11, wherein the second machine learning model further takes as input physiological information, and wherein the blood flow training set further comprises physiological information from at least one of the plurality of videos of other human subjects for which it is known whether each video is synthesized.

13. The system of claim 11, wherein determining the blood flow signals by the TOI module comprises determining a blood flow signal for each of a plurality of predetermined regions of interest (ROIs) of the human subject captured by the images based on the HC changes.

14. The system of claim 13, further comprising a profile module to decompose the blood flow signals outputted by the first machine learning model into a frequency profile and a phase profile, the frequency profile and the phase profile used as the input blood flow signals to the second machine learning model.

15. The system of claim 14, wherein the frequency profile comprises a frequency spectrum analysis per ROI.

16. The system of claim 15, further comprising a filter module to separately defined frequency passband signals over the frequency spectrum as the frequency profile, wherein each frequency passband signal comprises an individual 12th order Elliptical digital filter.

17. The system of claim 16, further comprising a combination module to combine discrete frequency passband signals as the frequency.

18. The system of claim 14, wherein the phase profile comprises a plurality of beat vectors, each beat vector comprising motion of a blood flow signal in a particular ROI relative to the blood flow signal in another ROI.

19. The system of claim 11, wherein the bit values from the set of bitplanes in the captured image sequence comprises the bit values that are determined to approximately maximize a signal-to-noise ratio (SNR).

20. The system of claim 11, wherein the second machine learning model outputs a statistical probability corresponding to a level of certainty of whether the blood flow patterns from the video are indicative of a synthesized video.

* * * * *